(12) United States Patent
Jobdevairakkam et al.

(10) Patent No.: US 7,884,227 B2
(45) Date of Patent: Feb. 8, 2011

(54) FELBAMATE WITH IMPROVED BULK DENSITY

(75) Inventors: Christopher Newton Jobdevairakkam, Plainsboro, NJ (US); Hero Velladurai, Plainsboro, NJ (US)

(73) Assignee: Navinta LLC, Ewing, NJ (US)

( * ) Notice: Subject to any disclaimer, the term of this patent is extended or adjusted under 35 U.S.C. 154(b) by 283 days.

(21) Appl. No.: 12/258,553

(22) Filed: Oct. 27, 2008

(65) Prior Publication Data

US 2009/0111871 A1      Apr. 30, 2009

Related U.S. Application Data

(60) Provisional application No. 60/982,885, filed on Oct. 26, 2007.

(51) Int. Cl.
C07C 269/04    (2006.01)
C07C 269/08    (2006.01)
A61K 31/27     (2006.01)

(52) U.S. Cl. .................................. 560/158; 514/483
(58) Field of Classification Search .................. None
See application file for complete search history.

(56) References Cited

U.S. PATENT DOCUMENTS 2,884,444 A * 4/1959 Berger et al. ................ 560/164
4,868,327 A    9/1989 Stiefel
4,978,680 A    12/1990 Sofia
4,982,016 A    1/1991 Choi
5,082,861 A    1/1992 Sofia
5,091,595 A    2/1992 Choi
5,500,484 A    3/1996 Iwasaki et al.
7,175,856 B2   2/2007 Ullah et al.
2008/0311162 A1 * 12/2008 Darmuzey et al. ........... 424/401

FOREIGN PATENT DOCUMENTS

WO    9406737 A1    3/1994
WO    9427941 A1    12/1994

OTHER PUBLICATIONS

Bulk Density—definition from wikipedia, the free encyclopedia retrieved from the internet via http://en.wikipedia.org/wiki/Bulk_density on Jun. 16, 2009; 2 pages.
Martin A. Thomas Ph.D; Tablets &Capsules: Powder Density in Solid Dosage Forms; Quantachrome Corporation 2005; 1 page.

* cited by examiner

*Primary Examiner*—Rosalynd Keys
(74) *Attorney, Agent, or Firm*—St. Onge Steward Johnston & Reens LLC

(57) ABSTRACT

A synthesis and purification of felbamate, an anticonvulsant, are provided. The product of the synthesis and purification is with high untapped and tapped bulk densities, which increase ease of handling and suitability for use in pharmaceutical formulations. The felbamate may be incorporated into pharmaceutical compositions that can be administered orally for treatment of epilepsy.

7 Claims, No Drawings

FELBAMATE WITH IMPROVED BULK DENSITY

PRIOR APPLICATIONS

This applications claims priority of U.S. Provisional Patent Application Ser. No. 60/982,885 filed Oct. 26, 2007.

FIELD OF THE INVENTION

The present invention relates to an improved synthetic process and a novel purification method to manufacture felbamate of high bulk density.

BACKGROUND OF THE INVENTION

Felbamate (2-phenyl-1,3-propanediol dicarbamate) is an anticonvulsant used in the treatment of epilepsy, as described in U.S. Pat. Nos. 4,978,680 and 5,082,861, which are incorporated by reference. Several syntheses of felbamate have been described, including the methods of U.S. Pat. Nos. 4,868,327, 4,982,016, 5,091,595 and 5,500,484, as well as WO 94/06737 and WO 94/27941, all of which are incorporated by reference. WO 94/06737 and WO 94/27941 teach a felbamate synthesis by reaction of 2-phenyl-1,3-propanediol with chlorosulfonyl isocyanate. This method is typical of those used to manufacture felbamate commercially.

However, a disadvantage of these processes is the production of felbamate with relatively high level of impurity. Because the average daily dosage of felbamate is about 600 mg, it is essential to control the formation of impurities in felbamate. Another disadvantage of process disclosed in WO 94/06737 and WO 94/27941 is that the process yields felbamate with a relatively low tapped bulk density, resulting in handling difficulties during processing and use. A material with a higher tapped bulk density is desirable during the manufacture of pharmaceuticals containing felbamate, particularly oral dosage forms. The oral suspension dosage form of felbamate, when made with felbamate of low bulk density, is very thick and difficult to deliver in desired administration. However, according to the present invention, the oral suspension dosage form of felbamate made with high bulk density felbamate obtained by the process of this invention is found to be free flowing and suitable for delivering the desired dosage administration.

SUMMARY OF THE INVENTION

A novel synthetic and purification procedure has been disclosed in the present invention that provides crystalline felbamate which has a desirable tapped bulk density, allowing for improved ease of handling during manufacture of pharmaceuticals and provides a product ideal for use in oral administration.

The invention discloses a method of synthesizing felbamate, comprising the steps of: (a) adding a solution of 2-phenyl-1,3-propanediol to a solution of chlorosulfonyl isocyanate while maintaining a temperature less than about −20° C. over a first period ranging from about 10 minutes to about 60 minutes; (b) maintaining temperature of the solution of 2-phenyl-1,3-propanediol and chlorosulfonyl isocyanate at less than about −20° C. for a second period ranging from about 30 to about 45 minutes while stirring; (c) adding water to the solution of 2-phenyl-1,3-propanediol and chlorosulfonyl isocyanate and increasing temperature to a range of about 20° C. to about 40° C.; (d) concentrating the solution of 2-phenyl-1,3-propanediol and chlorosulfonyl isocyanate after step (c); (e) adding water to the solution of 2-phenyl-1,3-propanediol and chlorosulfonyl isocyanate after step (d) and cooling to about 5° C. to 30° C.; and (f) isolating felbamate which precipitates from the solution of 2-phenyl-1,3-propanediol and chlorosulfonyl isocyanate. The solution of chlorosulfonyl isocyanate may be cooled to a temperature ranging from about −20° C. to about −40° C. before the solution of 2-phenyl-1,3-propanediol is added in step (a). Alternatively, the solution of chlorosulfonyl isocyanate is cooled to about −30° C. to about −40° C. before the solution of 2-phenyl-1,3-propanediol is added in step (a).

The invention also comprises a method for purifying felbamate, comprising the steps of: (a) dissolving the felbamate in a mixture comprising a solvent by heating the mixture to at least about 50° C. to form a solution; (b) cooling the solution to a range of about 40° C. to about 50° C.; (c) adding water to the solution from step (b) and cooling the solution to a range of about 0° C. to 10° C.; and (d) isolating the felbamate which has formed crystals. The solvent may be selected from the group consisting of ethanol, methanol, tetrahydrofuran, isopropanol, acetonitrile, water and mixtures thereof.

The felbamate which has formed crystals has a tapped bulk density ranging from about 0.35 gm/ml to about 0.6 gm/ml, about 0.4 gm/ml to about 0.6 gm/ml, preferably about 0.5 gm/ml. The felbamate crystals may be formulated into a pharmaceutical composition such as oral suspensions, capsules or tablets.

DETAILED DESCRIPTION OF THE INVENTION

As described by Thomas, *Tablets and Capsules: Powder Density in Solid Dosage Forms*, available at http://www.quantachrome.com/articles_pdf/tablets_capsules.pdf, both active and inactive (excipient) compounds are used in the manufacture of solid pharmaceuticals, including tablets. These compounds, usually in the form of crystalline solids and powders thereof, possess many properties or characteristics and exhibit certain behaviors as a result.

One important characteristic is tapped bulk density, or simply tapped (or tap) density, that is the maximum packing density of a powder (or blend of powders) achieved under the influence of well defined, externally applied forces (see, http://en.wikipedia.org/wiki/Bulk_density). The minimum packed volume thus achieved depends on a number of factors including particle size distribution, true density, particle shape and cohesiveness due to surface forces including moisture. Therefore, the tap density of a material can be used to predict both its flow properties and its compressibility. These two parameters are important in the overall tabletting process, which requires that loose powders be compacted into a durable solid form with the correct mechanical strength, porosity and dissolution characteristics. These parameters are also important in the formation of oral suspensions, which ideally contain particles of high bulk density, enabling even dispersion of the particles throughout the suspension after shaking and before consumption.

Preferably, the tapped bulk density of felbamate for use in tablets or oral suspensions is about 0.35 to about 0.65 gm/ml. More preferably, the tapped bulk density is about 0.40 to about 0.60 gm/ml.

2-Phenyl-1,3-propanediol used for making felbamate by the process of this invention was prepared by the process disclosed in WO 94/06737 and WO 94/27941.

WO 94/06737 and WO 94/27941 disclose that, to synthesize felbamate, a solution of chlorosulfonyl isocyanate is added to a suspension of 2-phenyl-1,3-propanediol at about 10° C. to 25° C. One of the major disadvantages of this process is that 2-phenyl-1,3-propanediol remains in reaction suspension at 10° C. to 25° C., causing inconsistent reaction dynamics upon scale up, and rendering the process less useful in commercial manufacturing. In addition, the felbamate obtained by this process contains an unknown impurity of about 3 to 5 percent.

According to the present invention, when a solution of 2-phenyl-1,3-propanediol is added to a solution of chlorosulfonyl isocyanate, as compared with reactions disclosed in the prior art, WO 94/06737 and WO 94/27941 (see above), over a period of about at least 10 to 60 minutes, felbamate containing less than 0.2% of the unknown impurity is produced. It is also essential to keep both reagents (2-phenyl-1,3-propanediol and chlorosulfonyl isocyanate) in solution to promote the reaction at −20° C. to −40° C. The combination of solvent mixtures necessary to keep 2-phenyl-1,3-propanediol in solution can be chosen by one of ordinary skill in the art without undue experimentation.

In an embodiment of the synthetic procedure of this invention, the chlorosulfonyl isocyanate is dissolved in toluene before the reaction and the 2-phenyl-1,3-propanediol dissolved in a mixture of tetrahydrofuran and toluene. Other embodiments may utilize different solvents for either reagent, including at least toluene, tetrahydrofuran, benzene, xylene, ethyl acetate, monoglyme, diglyme, dioxane, acetonitrile and suitable combinations thereof. Several different embodiments of the present invention are illustrated below in the following examples.

Felbamate may also be purified by the methods of the present invention. For example, felbamate is dissolved in a mixture of water and methanol by heating and the resulting solution filtered through a filtration system at temperatures of about 70° C. The filtrate (the liquid that passes through the filtration system) is stirred and gradually cooled in two steps, first to about 40° C. to about 45° C., during which time felbamate begins to recrystallize, and second to about 2° C. to about 5° C. after addition of water. After water has been added, the mixture is stirred for an hour before the felbamate is isolated. In an embodiment of the procedure, the isolated product is further dried under vacuum at about 35° C. to about 38° C.

Other solvents may be used, including differing ratios of methanol and water or other solvent systems, including at least one water miscible solvent such as, ethanol, isopropanol, acetonitrile, water or mixtures thereof. The temperature at which the dissolution and filtration must occur will vary with the solvent system chosen and can be determined without undue experimentation by one of ordinary skill in the art. One embodiment of this purification procedure is illustrated below in Example 3.

Water alone may also be used as solvent to dissolve felbamate at about 70° C. Upon cooling the solution, felbamate precipitates out. Once precipitated, the felbamate can be isolated by filtration, centrifugation or decanting the supernatant liquid. Once isolated, the felbamate can be dried to remove the solvent.

In one embodiment, the purified felbamate was dried under vacuum and milled to obtain desired particle size distribution of about 90% less than 100 µm, preferably 90% less than 70 µm, more preferably 90% less than 40 µm.

The synthetic and purification procedures of this invention produce felbamate crystals with desirable tapped bulk density properties. Typically, the product has a tapped bulk density of ranging from 0.35 gm/ml to about 0.6 gm/ml, about 0.4 gm/ml to about 0.6 gm/ml, and preferably about 0.5 gm/ml.

A therapeutically effective amount of felbamate prepared by the synthetic or purification procedures of this invention may be incorporated into a pharmaceutical composition for the treatment of epilepsy.

A formulation of a pharmaceutical composition suitable for oral administration may be in the form of a discrete solid dosage unit. Solid dosage units include, for example, a tablet, a caplet, a hard or soft capsule, a cachet, a troche or a dissolvable tab. Each solid dosage unit contains a predetermined amount of the drug, for example a unit dose or fraction thereof. Other formulations suitable for administration include, but are not limited to, a powdered or granular formulation.

A tablet comprising the drug may be made, for example, by compressing or molding the drug, optionally containing one or more additional components. Compressed tablets may be prepared by compressing, in a suitable device, the drug in a free-flowing form such as a powder or granular preparation, optionally mixed with one or more of a binder, a lubricant, a glidant, an excipient, a surface active agent and a dispersing agent. Molded tablets may be made by molding, in a suitable device, a mixture of the drug, a pharmaceutically acceptable carrier, and at least sufficient liquid to moisten the mixtures. Tablets may further comprise a sweetening agent, a flavoring agent, a coloring agent, a preservative, or some combination of these in order to provide pharmaceutically elegant and palatable preparations.

Hard capsules comprising the pharmaceutical agent may be made using a physiologically degradable composition, such as gelatin. Such hard capsules comprise the active ingredient, and may further comprise additional components including, for example, an inert solid diluent. Soft gelatin capsules comprising the pharmaceutical agent may be made using a physiologically degradable composition, such as gelatin. Such soft capsules comprise the pharmaceutical agent, which may be mixed with water or an oil medium.

Powdered and granular formulations may be prepared using known methods or methods to be developed. Such formulations may be administered directly to a subject, or used, for example, to form tablets or to fill capsules. Powdered or granular formulations may further comprise one or more of a dispersing or wetting agent, a suspending agent, and a preservative. Additional excipients, such as fillers and sweetening, flavoring, or coloring agents, may also be included in these formulations.

Tablets and pills can additionally be prepared with release-controlling coatings. The coating may be colored with a pharmaceutically accepted dye. The amount of dye and other excipients in the coating liquid may vary. The coating liquid generally comprises film-forming polymers such as hydroxypropyl cellulose, hydroxypropylmethyl cellulose, cellulose ester or ether, in acrylic polymer or a mixture of polymers. The coating solution is generally an aqueous solution that may further comprise propylene glycol, sorbitan monooleate, sorbic acid, or fillers such as titanium dioxide, a pharmaceutically acceptable dye.

The solid pharmaceutical compositions may include diluents. Diluents for solid compositions include, for example, microcrystalline cellulose (e.g. AVICEL®), silicified microcrystalline cellulose (http://www.drugdeliverytech.com/cgi-bin/articles.cgi?idArticle=109), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. EUDRAGIT®), potassium chloride, powdered cellulose, sodium chloride, sorbitol and talc.

Solid pharmaceutical compositions may include binders, e.g., acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate and starch.

Disintegrants such as alginic acid, carboxymethylcellulose calcium, carboxymethylcellulose sodium (e.g. AC-DI-SOL®, PRIMELLOSE®), colloidal silicon dioxide, croscarmellose sodium, crospovidone (e.g. KOLLIDON®, POLYPLASDONE®), guar gum, magnesium aluminum silicate, methyl cellulose, polacrilin potassium, powdered cellulose, pregelatinized starch, sodium alginate, sodium starch glycolate (e.g. EXPLOTAB®), hydroxypropylcellulose, methylcellulose, povidone or starch may be added to the solid pharmaceutical compositions. Glidants, such as, colloidal silicon dioxide, magnesium trisilicate, powdered cellulose, starch, talc and tribasic calcium phosphate may also be added.

Other pharmaceutical additives include: (i) lubricants such as magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate; (ii) flavoring agents and flavor enhancers such as maltol, vanillin, ethyl vanillin, menthol, citric acid, fumaric acid ethyl maltol, and tartaric acid; and, (iii) pharmaceutically acceptable colorants.

Another pharmaceutical dosage form is the oral suspension, in which particles of the active ingredient are dispersed in a liquid in which the active ingredient is insoluble. Oral suspensions typically use water as the suspending liquid, but the liquid used can be any liquid suitable for consumption, including, without limitation, ethanol-water solvent mixtures. Oral suspensions may also contain one or more flavoring, sweetening, or masking agents in order to mask the taste of an unpalatable active ingredient, as described in U.S. Pat. No. 7,175,856, which is incorporated by reference.

The felbamate of this invention may be utilized in tablet dosage forms from 100 to 1000 mg, more preferably 400 and 600 mg, and in oral suspensions from 100 mg/5 ml to 1000 mg/5 ml, preferably 600 mg/5 ml oral suspension.

To describe the preferred embodiments of novel synthesis and purification methods more particularly, the following non-limiting examples are presented.

EXAMPLE 1

Synthesis of Felbamate

A solution of 67 gm (0.44 moles) of 2-phenyl-1,3-propanediol, which had been dissolved in a mixture of 67 ml of tetrahydrofuran and 67 ml of toluene at room temperature (approximately, 20° C. to 25° C.), was added over a period of about 10 to 60 minutes to a solution of 600 ml of dry toluene and 140 ml of chlorosulfonyl isocyanate. The reaction vessel containing the combined solutions was maintained at temperatures ranging from about −20° C. to −40° C., −30° C. to −40° C., preferably −35° C. to −40° C. The reaction was stirred for 30 to 45 minutes at about −30° C. to about −40° C. and the reaction monitored by high performance liquid chromatography (HPLC). Upon completion of reaction, water (1340 ml) was charged into the reaction mixture, increasing the temperature in the reaction vessel to about 20° C. to about 40° C. The temperature of the reaction was then raised further to about 45° C. to about 60° C. and the solvent distilled under vacuum until the reaction mixture became homogenous or its volume reduced to about 60 to about 80 percent of the original volume of the reaction mixture. Water (670 ml) was then added to the reaction mixture, which was cooled to about 2° C. to about 5° C. and stirred for an hour at that temperature. The product was then filtered and washed with water.

EXAMPLE 2

Synthesis of Felbamate

A solution of 67 gm (0.44 moles) of 2-phenyl-1,3-propanediol, which had been dissolved in a mixture of 80 ml of acetonitrile and 65 ml of toluene at room temperature, was added to a mixture of 600 ml of dry toluene and 140 ml of chlorosulfonyl isocyanate placed in a dry reaction vessel maintained at −20° C. to −30° C. over a period of about 10 to 60 minutes. The reaction mixture was stirred for 30 to 45 minutes at about 30° C. to about 40° C. and the reaction progress monitored by high performance liquid chromatography (HPLC). Upon completion of reaction, water (1340 ml) was charged into the reaction mixture, increasing the reaction temperature to about 20° C. to about 40° C. The temperature of the reaction vessel was raised to about 45° C. to about 60° C. and the solvent distilled under vacuum until the reaction mixture was homogenous or its volume reduced to about 60 to 80 percent of the original volume of the reaction mixture. Water (670 ml) was then added to the reaction mixture, which was cooled to about 2° C. to about 5° C. and stirred for an hour at that temperature. The product was then filtered and washed with water.

EXAMPLE 3

Purification of Felbamate using Methanol-Water

About 100 gm of felbamate was added to the flask containing 500 ml methanol and about 100 to 200 ml water. The contents were heated to at least about 70° C. This temperature was maintained until the contents became a clear solution (about 15 minutes). This solution was filtered at least at about 70° C. to remove any extraneous particles. The filtrate was cooled to about 40° C. to about 45° C. and then stirred for about 30 minutes, during which time felbamate precipitated. Water (500 ml) was added to the mixture over 30 minutes. The mixture was cooled to about 2° C. to about 5° C. and stirred for about 60 minutes at that temperature. The felbamate precipitated from the mixture was isolated by filtration and washed with water. The product was dried under vacuum at about 30 to about 60° C., preferably between 30° C. to 40° C., for about 6 hours to yield 97 gm of felbamate (0.407 moles, 92% yield, tapped bulk density 0.5 gm/ml).

EXAMPLE 4

Purification of Felbamate using Acetonitrile-Water

About 100 gm of felbamate was added to a flask containing 500 ml of acetonitrile and 100 ml water. The contents were heated to about 50° C. This temperature was maintained until the contents became a clear solution (about 15 minutes). This solution was filtered at least at about 50° C. to remove any extraneous particles. The filtrate was cooled to about 40° C. and stirred for about 30 minutes, during which time felbamate precipitated. Water (600 ml) was added to the mixture over 30 minutes and the mixture cooled to about 0° C. to about 5° C. and stirred for about 60 minutes at that temperature. The felbamate precipitated from the mixture was isolated by filtration and washed with water. The product is dried under vacuum at about 30° C. to about 60° C., preferably between 30° C. to 40° C., for about 6 hours to yield 97 gm of felbamate (0.407 moles, 92% yield, tapped bulk density 0.55 gm/ml).

EXAMPLE 5

Purification of Felbamate using Tetrahydrofuran-Water

About 100 gm of felbamate was added to the flask containing 500 ml of tetrahydrofuran and 150 ml water. The contents were heated to at about 60° C. This temperature was maintained until the contents become a clear solution (about 15 minutes). This solution was filtered at least at about 60° C. to remove any extraneous particles. The filtrate was cooled to about 40° C. and stirred for about 30 minutes, during which time felbamate precipitated. Water (600 ml) was added to the mixture over 30 minutes and the mixture cooled to about 0° C. to about 5° C. and stirred for about 60 minutes at that temperature. The felbamate precipitated from the mixture was isolated by filtration and washed with water. The product was dried under vacuum at about 30° C. to about 60° C. preferably between 30° C. to 40° C. for about 6 hours to yield 93 gm of felbamate (tapped bulk density 0.4 gm/ml).

EXAMPLE 6

Purification of Felbamate using Isopropanol-Water

About 100 gm of felbamate was added to the flask containing 500 ml of isopropanol and 100 ml water. The contents were heated to at about 75° C. This temperature is maintained until the contents became a clear solution (about 15 minutes). This solution was filtered at least at about 70° C. to remove any extraneous particles. The filtrate was cooled to about 40° C. and stirred for about 30 minutes, during which time felbamate precipitated. Water (500 ml) was added to the mixture over 30 minutes and the mixture was cooled to about 0° C. to about 5° C. and stirred for about 60 minutes at that temperature. The felbamate precipitated from the mixture was isolated by filtration and washed with water. The product was dried under vacuum at about 30° C. to about 60° C., preferably between 30° C. to 40° C., for about 6 hours to yield 95 gm of felbamate (tapped bulk density 0.54 gm/ml). The felbamate thus obtained was milled to get the desired particle size distribution of about 90% less than 100 μm, preferably 90% less than 70 μm, more preferably 90% less than 40 μm.

EXAMPLE 7

Purification of Felbamate using Water

About 25 gm of felbamate was added to the flask containing 1000 ml of water. The contents were heated to at about 80° C. This temperature was maintained until the contents became a clear solution (about 15 minutes). This solution was filtered at least at about 75° C. to remove any extraneous particles. The filtrate was cooled to about 40° C. and stirred for about 30 minutes, during which time felbamate precipitated. Water (600 ml) was added to the mixture over 30 minutes and the mixture cooled to about 5° C. and stirred for about 60 minutes at that temperature. The felbamate precipitated from the mixture was isolated by filtration and washed with water. The product was dried under vacuum at about 60° C. for about 12 hours to yield 20 gm of felbamate (tapped bulk density 0.35 gm/ml).

EXAMPLE 8

Bulk Density Determination of Felbamate

Felbamate (1.211 gm) purified by the above process (Example 3) was poured into a 10 ml graduated cylinder. The untapped volume of felbamate was 3.5 ml, resulting in an untapped bulk density of 0.35 gm/ml which was greater than the untapped bulk density of felbamate prepared by other methods (see below, Examples 9 and 10). The graduated cylinder was tapped until the felbamate (50 taps) no longer settled. The volume of felbamate after tapping was 2.2 ml, resulting in a tapped bulk density of 0.55 gm/ml.

EXAMPLE 9

Bulk Density of Felbamate Prepared by the Method of WO 94/06737

Felbamate (0.972 gm) synthesized by the process disclosed in WO 94/06737 was poured into a 10 ml graduated cylinder. The untapped volume of felbamate was 5.1 ml, resulting in an untapped bulk density of 0.19 gm/ml. The graduated cylinder was tapped until the felbamate (50 taps) no longer settled. The volume of felbamate after tapping was 3.2 ml, resulting in a tapped bulk density of 0.30 gm/ml.

EXAMPLE 10

Bulk Density of Felbamate Prepared by the Method of U.S. Pat. No. 4,868,327

Felbamate (2 gm) synthesized by the process disclosed in U.S. Pat. No. 4,868,327 was purified by adding to 20 ml of methanol, heating the methanol to reflux to obtain a clear solution, cooling the solution to room temperature over three hours with stirring, and isolating the felbamate by filtration and drying under vacuum at 50° C. Felbamate (0.927 gm) purified by this process was poured into a 10 ml graduated cylinder. The untapped volume of felbamate was 6.5 ml, resulting in an untapped bulk density of 0.14 gm/ml. The graduated cylinder was tapped until the felbamate (50 taps) no longer settled. The volume of felbamate after tapping was 2.9 ml, resulting in a tapped bulk density of 0.32 gm/ml.

TABLE I

Bulk Density Data of Felbamate Obtained by Various Processes.

| Felbamate | Weight, gm | Untapped volume, ml | 50 tapped volume, ml | Untapped bulk density, ml | Tapped bulk density, ml |
|---|---|---|---|---|---|
| Purification process as disclosed in Example 3 | 1.211 | 3.5 | 2.2 | 0.35 | 0.55 |
| WO 94/06737 | 0.972 | 5.1 | 3.2 | 0.19 | 0.30 |
| U.S. Pat. No. 4,868,327 | 0.927 | 6.5 | 2.9 | 0.14 | 0.32 |

It should be understood that the above examples are illustrative only of the best mode of the invention herein disclosed. Given the present disclosure, numerous variations will occur to those skilled in the art. The invention incorporates modifications, substitutions and changes within the scope of one of ordinary skill in the art. In some instances, some features of the invention will be employed without a corresponding use of other features. All references cited in this specification, and their references, are incorporated by reference herein in their entirety where appropriate for teachings of additional or alternative details, features, and/or technical background.

What we claim is:

1. A method of synthesizing felbamate, comprising the steps of:
   (a) adding a solution of 2-phenyl-1,3-propanediol to a solution of chlorosulfonyl isocyanate while maintaining a temperature at less than about −20° C. over a first period ranging from about 10 minutes to about 60 minutes;
   (b) maintaining temperature of the solution of 2-phenyl-1,3-propanediol and chlorosulfonyl isocyanate at less than about −20° C. for a second period ranging from about 30 minutes to about 45 minutes while stirring;
   (c) adding water to the solution of 2-phenyl-1,3-propanediol and chlorosulfonyl isocyanate and increasing the temperature to a range of about 20° C. to about 40° C.;
   (d) concentrating the solution of 2-phenyl-1,3-propanediol and chlorosulfonyl isocyanate after step (c);
   (e) adding water to the solution of 2-phenyl-1,3-propanediol and chlorosulfonyl isocyanate after step (d) and cooling to about 5° C. to 30° C.; and
   (f) isolating felbamate which precipitates from the solution of 2-phenyl-1,3-propanediol and chlorosulfonyl isocyanate.

2. The method of claim 1 where the solution of chlorosulfonyl isocyanate is cooled to about −20° C. to about −40° C. before the solution of 2-phenyl-1,3-propanediol is added in step (a).

3. The method of claim 1 where the solution of chlorosulfonyl isocyanate is cooled to about −30° C. to about −40° C. before the solution of 2-phenyl-1,3-propanediol is added in step (a).

4. A method for purifying felbamate prepared according to the method of claim 1, comprising the steps of:
   (a) dissolving the felbamate in a mixture comprising a solvent by heating the mixture to at least about 50° C. to form a solution;
   (b) cooling the solution to a range of about 40° C. to about 50° C.;
   (c) adding water to the solution from step (b) and cooling the solution to a range of about 0° C. to 10° C.; and
   (d) isolating the felbamate which has formed crystals.

5. The method of claim 4 where the solvent is selected from the group consisting of ethanol, methanol, tetrahydrofuran, isopropanol, acetonitrile, water and mixtures thereof.

6. The method of claim 4 where the felbamate crystals have a tapped bulk density ranging from about 0.35 gm/ml to about 0.6 gm/ml.

7. The method of claim 6 where the tapped bulk density ranges from about 0.4 gm/ml to about 0.6 gm/ml.

* * * * *